(12) United States Patent
Koch et al.

(10) Patent No.: US 7,890,268 B2
(45) Date of Patent: Feb. 15, 2011

(54) DE-NOVO SEQUENCING OF NUCLEIC ACIDS

(75) Inventors: Thomas Koch, Penzberg (DE); Roderic Fuerst, Penzberg (DE); Uwe Kobold, Weilheim (DE); Dieter Heindl, Paehl (DE); Herbert von der Eltz, Weilheim (DE); David Gelfand, Oakland, CA (US); Ivo Gut, Paris (FR); Christoph Steinbeck, Düren (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 204 days.

(21) Appl. No.: 11/304,448

(22) Filed: Dec. 14, 2005

(65) Prior Publication Data

US 2006/0141516 A1    Jun. 29, 2006

Related U.S. Application Data

(60) Provisional application No. 60/639,953, filed on Dec. 28, 2004.

(51) Int. Cl.
  *G06F 19/00*   (2006.01)
  *G01R 23/16*   (2006.01)
(52) U.S. Cl. ........................ 702/20; 250/283
(58) Field of Classification Search ................ None
  See application file for complete search history.

(56) References Cited

U.S. PATENT DOCUMENTS 5,939,292 A * 8/1999 Gelfand et al.
6,051,378 A * 4/2000 Monforte et al.

OTHER PUBLICATIONS

Oberacher et al. Automated De Novo Sequencing of Nucleic Acids by Liquid Chromatography-Tandem Mass Spectrometry. Journal of the American Society for Mass Spectrometry vol. 15, pp. 32-42 (2003).*
Oberacher et al. Comparative Sequencing of Nucleic Acids by Liquid Chromatography-Tandem Mass Spectrometry. Analytical Chemistry vol. 74 pp. 211-218 (2002).*
Fogel An introduction to Simulated Evolutionary Optimization. IEEE Transactions on Neural Networks vol. 5, pp. 3-14 (1994).*
Keith et al. A simulated annealing algorithm for finding consensus sequences. Bioinformatics vol. 18 pp. 1494-1499 (2002).*
Oberacher et al. Re-sequencing of multiple single nucleotide polymorphisms by liquid chromatography-electrospray ionization mass spectrometry Nucleic Acids Research vol. 30 p. e67 (2002).*
Stepniewski, Slawomir W., et al., 1997, "Pruning Backpropogation Neural Networks Using Modern Stochastic Optimisation Techniques", Neural Comput & Applic, 5:76-98.

* cited by examiner

*Primary Examiner*—John S Brusca
(74) *Attorney, Agent, or Firm*—Charles M. Doyle; Olga Kay; Vivien Banholzer

(57) ABSTRACT

The present invention is directed to an improved analysis procedure for the comparative sequencing of nucleic acids using multistage mass spectrometry. More precisely, the invention is directed to a method enabling the de-novo sequencing of nucleic acid molecules using multistage mass spectrometry.

26 Claims, 10 Drawing Sheets

| Oligo Sequence | MW mono [Da] | charge state -2 [Da] | MW av [Da] | charge state -2 [Da] |
|---|---|---|---|---|
| CCTCA | 1422.28 | 710.1 | 1423.00 | 710.5 |
| GGGCA | 1527.30 | 762.6 | 1528.06 | 763.0 |
| TGCTCA | 1766.34 | 882.2 | 1767.22 | 882.6 |
| CCGGCA | 1776.34 | 887.2 | 1777.22 | 887.6 |
| GTGCCCA | 2080.39 | 1039.2 | 2081.42 | 1039.7 |
| GGTCTCA | 2095.39 | 1046.7 | 2096.43 | 1047.2 |
| CCCTCCCA | 2289.42 | 1143.7 | 2290.55 | 1144.3 |
| GGCGCCCA | 2394.44 | 1196.2 | 2395.62 | 1196.8 |

Template PCR Product 87bp (SEQ ID NO:2)
CTGGGAGGGTGTGTCTCAGTGTCTATGGCTGTGGTTCGGTATAAGTCTGAGCATGTCTGCCAGGGTGTATTTGTGCCTGTATGTGCG
GACCCTCCCACACAGAGTCACAGATACCGACACCAAGCCATATTCAGACTCGTACAGACGGTCCCACATAAACACGGACATACACGC Ribo A Forward Extension 87bp <u>CTGGGAGGGTGTGTCTCAGT</u>GTCTATGGCTGTGGTTCGGTATAAGTCTGAGCATGTCTGCCAGGGTGTATTTGTGCCTGTATGTGCG (SEQ ID NO:2)

|  |  | adn<br>[Da] | adn+arn+phos<br>[Da] |
|---|---|---|---|
| forward primer | CTGGGAGGGTGTGTCTCAGT<br>(SEQ ID NO:3) | 6250.08 |  |
| forward primer +<br>ext | CTGGGAGGGTGTGTCTCAGTGTCTA<br>(SEQ ID NO:5) | 7760.3 | 7887.1 |
| F | TGGCTGTGGTTCGGTA<br>(SEQ ID NO:6) | 4959.4 | 5056.3 |
| F | GTCTGA | 1807.3 | 1904.3 |
| F | GCA | 869.7 | 966.6 |
| F | TGTCTGCCA | 2689.9 | 2786.8 |
| F | GGGTGTA | 2176.5 | 2273.5 |
| F | TTTGTGCCTGTA<br>(SEQ ID NO:7) | 3642.5 | 3739.5 |
| F | TGTGCG | 1823.3 |  |

Ribo A Reverse Extension 87bp

GACCCTCCCACACAGAGTCACAGATACCGACACCAAGCCATATTCAGACTCGTACAGACGGTCCC<u>ACATAAACACGGACATACACGC</u>

(SEQ ID NO:2)

|  |  | adn | adn+arn+phos |
|---|---|---|---|
| reverse primer | CGCACATACAGGCACAAATAC<br>(SEQ ID NO:4) | 6407.25 |  |
| reverse primer +<br>ext | CGCACATACAGGCACAAATACA<br>(SEQ ID NO:8) | 6690.6 | 6817.5 |
| R | CCCTGGCA | 2370.6 | 2467.6 |
| R | TGCTCA | 1767.3 | 1864.2 |
| R | CTTA | 1148.8 | 1245.8 |
| R | CCGA | 1158.8 | 1255.8 |
| R | CCA | 829.6 | 926.6 |
| R | GCCA | 1158.8 | 1255.8 |
| R | CTGA | 1173.9 | 1270.8 |
| R | CCCTCCCA | 2290.6 | 2387.6 |

Figure 14

Sequence of riboPCR Product 87bp

CTGGGAGGGTGTGTCTCAGTGTCTATGGCTGTGGTTCGGTATAAGTCTGAGCATGTCTGCCAGGGTGTATTTGTGCCTGTATGTGCG
GACCCTCCCACACAGAGTCACAGATACCGACACCAAGCCATATTCAGACTCGTACAGACGGTCCCACATAAACACGGACATACACGC (SEQ ID NO:2)

| | | adn [Da] | adn+arn+phos [Da] |
|---|---|---|---|
| R | CCA | 829.6 | 926.6 |
| F | GCA | 869.7 | 966.6 |
| R | CTTA | 1148.8 | 1245.8 |
| R | GCCA | 1158.8 | 1255.8 |
| R | CCGA | 1158.8 | 1255.8 |
| R | CTGA | 1173.9 | 1270.8 |
| F | TGTGCG | 1823.3 | |
| R | TGCTCA | 1767.3 | 1864.2 |
| F | GTCTGA | 1807.3 | 1904.3 |
| F | GGGTGTA | 2176.5 | 2273.5 |
| R | CCCTCCCA | 2290.6 | 2387.6 |
| R | CCCTGGCA | 2370.6 | 2467.6 |
| F | TGTCTGCCA | 2689.9 | 2786.8 |
| F | TTTGTGCCTGTA (SEQ ID NO:7) | 3642.5 | 3739.5 |
| F | TGGCTGTGGTTCGGTA (SEQ ID NO:6) | 4959.4 | 5056.3 |
| Reverse Primer +ext | CGCACATACAGGCACAAATACA (SEQ ID NO:8) | 6690.6 | 6817.5 |
| Forward Primer +ext | CTGGGAGGGTGTGTCTCAGTGTCTA (SEQ ID NO:5) | 7760.3 | 7857.2 |

Figure 15

DE-NOVO SEQUENCING OF NUCLEIC ACIDS

PRIORITY APPLICATION

This application claims the benefit of priority under 35 U.S.C. §119(e) of U.S. Provisional Application No. 60/639,953, filed Dec. 28, 2004, the contents of which are hereby incorporated by reference.

FIELD OF THE INVENTION

The present invention relates to the field of nucleic acid analysis. In particular, the present invention is directed to a method for sequencing of nucleic acids. More particularly, the present invention is directed to a method, a kit and a system for de-novo sequencing of nucleic acids using mass spectrometry.

BACKGROUND OF THE INVENTION

The rapid sequencing of nucleic acids (NA) in a biological sample in order to characterize single nucleotide polymorphisms (SNP), complex mutations or for de-novo sequencing is of growing interest in the art. Such sequencing can be performed directly with biological samples containing sufficient amounts of the target nucleic acids or after the amplification of the NA within the biological sample.

Sequencing of nucleic acids is mainly performed using the Sanger method and analysis with capillary electrophoresis (Smith A J H Methods Enzymol. 65 (1980) 560-580). The Sanger sequencing method is based on a controlled termination of the enzymatic replication process and the subsequent analysis of the chain termination products. The chain termination products are produced with 4 different amplification reactions, wherein for each amplification reaction one of the normal nucleotides is partially replaced (1-4%) by the corresponding didesoxynucleotide (ddNTP) labeled with a fluorescence dye in order to terminate the replication process after the random incorporation of said ddNTP. These 4 different amplification reactions may be performed simultaneously in one preparation using different fluorescence dyes for each of the 4 terminating nucleic acid bases or separately with 4 individual preparations, whereas one fluorescence dye is sufficient. Although the classical Sanger sequencing of NAs using electrophoretic separation of chain termination products is well established, this method is time consuming, non-multiplexable and requires labeled ddNTPs together with expensive enzymes. On the other hand, the Sanger method can be used for de-novo sequencing.

An alternative to the classical Sanger sequencing with electrophoresis is the sequencing via mass spectrometry (MS), a technique that does not suffer from the problems mentioned above. In the literature, one can find review articles summarizing the genotyping of SNPs by mass spectrometry (Tost et al Mass Spec Review 21(6) (2002) 388-418) or the use of mass spectrometry in genomics (Meng et al Biomol. Eng. 21(1) (2004) 1-13). The sequencing on the basis of mass spectrometry is known mainly with three different methods that are used predominantly: a) Ladder Sequencing (Exonuclease digest followed by determination of the molecular weight (MW) of the products (Smirnov I P et al. Anal. Biochem. 238 (1996) 19-25)), b) Sanger Sequencing followed by determining the MWs of the chain termination products (Kirpekar F et al. Nucl. Acids Research 26 (11) (1998) 2554-2559) and c) Sequencing by collision induced dissociation, the so called CID-fragmentation (WO 03/025219 A2; Oberacher et al J. Am. Soc. Mass Spec 15(1) (2004) 32-42).

The mass spectrometric analysis involving CID-fragmentation is also called tandem mass spectrometry or MS/MS technique (or more general $MS^n$). Tandem mass spectrometry comprises isolation of a parent molecular ion followed by fragment formation in the gas phase via collision or resonance activation and determining the molecular weights of the fragments. Application of tandem mass spectrometry for peptide sequence analysis is well known in the literature (U.S. Pat. No. 6,017,693).

In case of nucleic acids, the comparison of theoretical fragments from a given reference sequence with the experimental fragment mass spectra allows for identification of the NA. The reference sequence is systematically altered through permutation until a best fit between experimental and theoretical data is obtained. (WO 03/025219 A2, Oberacher et al. Nucleic Acids Research 30(14) (2002) e67). Using this approach, it is possible to reliably verify sequences (re-sequencing) or to specifically detect oligonucleotides in a biological sample.

However, the major problem of sequencing with MS lies in the fact that using the described methods only rather short sequence lengths can be covered. Using the MALDI (matrix-assisted laser desorption)—Sanger method a maximum of 30 bp can be sequenced. This is also true for the method according to U.S. Pat. No. 6,017,693, where problems are eminent already at NA lengths of 10 bp. The sequence verification according to WO 03/025219 A2 shows problems for oligonucleotides longer than 40 to 60 bp. Additionally, the comparison of theoretical data for all possible sequences with the experimental data for de-novo sequencing becomes time consuming with increasing nucleic acid length.

If longer target nucleic acids have to be analyzed, several different approaches are known in the art that offer the opportunity of fragmenting nucleic acids in a controlled fashion.

Controlled fragmentation of nucleic acids may be realized using base specific reagents, like e.g. digestion or restriction enzymes. In case of ribonucleic acids, several RNAses are known that are able to cleave the target molecules, e.g. the G-specific RNAse $T_1$ or A-specific RNAse $U_1$. Dicer enzymes (RNAseIII family) cut RNA into well defined pieces of about 20 bases. In case of DNA, it is possible to use e.g. the uracil-DNA-glycosylase (UDG) or restriction endonucleases that recognize a specific base sequence and cut within or nearby this region. Nick-endonucleases can be used to cut only one strand of a dsDNA double helix.

As an alternative, Gelfand et al (U.S. Pat. No. 5,939,292) introduced a thermostable polymerase having reduced discrimination against ribonucleotides (NTPs or ribo-NTPs or ribo-bases). After an amplification step with said thermostable polymerase, the amplification product comprises a mixture of incorporated deoxyribonucleotides (dNTP) and NTPs providing the opportunity to use a simple alkaline hydrolysis step for the controlled fragmentation at the ribo-base positions. The resulting fragmentation products may be analyzed afterwards using electrophoresis in order to gain information of the nucleic acid sequence.

A fragmentation-based mass spectrometric method for the analysis of sequence variations is disclosed in WO 2004/050839. The WO 2004/097369 of the same applicant discloses a mass spectrometric method for the analysis and sequencing of biomolecules by fragmentation. The U.S. Pat. No. 6,468,748 B1 of Genetrace Systems Inc. describes a method for the analysis of biomolecules comprising mass spectrometry and a fragmentation step. U.S. Pat. No. 6,777,188 B1 discloses a method for genotyping a diploid organism comprising a comparison of masses and a cleaving step at modified nucleotides. Methexis Inc. describes a sequence analysis based on mass spectrometry, a cleavage reaction and the comparison with reference nucleic acids (WO 00/66771).

BRIEF SUMMARY OF THE INVENTION

Thus, the invention is directed to an improved analysis procedure for the comparative sequencing of nucleic acids using multistage mass spectrometry. More precisely, the invention is directed to a method enabling the de-novo sequencing of nucleic acid molecules using multistage mass spectrometry.

One subject matter of the present invention is a method for the sequencing of a target nucleic acid comprising:
a) performing a multistage mass spectrometry, comprising
  i) ionizing said target nucleic acid,
  ii) measuring the mass of the ionized target nucleic acid,
  iii) determining the base composition corresponding to the mass of said ionized target nucleic acid,
  iv) fragmenting said ionized target nucleic acid by a collision induced dissociation (CID) and
  v) measuring the corresponding mass spectrum of the CID fragments, and
b) comparing the measured CID mass spectrum of the target nucleic acid measured in step v) with a plurality of calculated CID mass spectra, wherein each of said calculated CID mass spectra correspond to a base sequence having the base composition determined in step iii),
  wherein the comparison of the measured CID mass spectrum with the calculated CID mass spectra is performed by an optimization algorithm, wherein said optimization algorithm compares said measured CID mass spectrum successively with said plurality of calculated CID mass spectra and determines a respective score value for each comparison, said score value representing the degree of consistency between said measured CID mass spectrum and said calculated CID mass spectra, and wherein the base sequence corresponding to the calculated CID mass spectra yielding the best score value is selected as the base sequence of said target nucleic acid.

There are several procedures for nucleic acid analysis that are frequently named "sequencing of nucleic acid" in the art, e.g. genotyping, re-sequencing, de-novo sequencing and comparative sequencing. Genotyping summarizes all processes of assessing genetic variation present in an individual. The most common type of genetic variation is the single nucleotide polymorphism (SNP). Therefore, genotyping determines the individual SNP pattern of an individual. The discovery of SNPs is in general performed with a re-sequencing approach, wherein a previously sequenced site is re-sequenced in order to find genetic variations. In case of de-novo sequencing, an unknown sequence is determined. In the majority of cases, the sequencing is performed with a comparative sequencing approach. Here, the experimental result of the target nucleic acid under investigation is compared with theoretical data or with the experimental result of reference molecules in order to identify the best match or to determine the level of agreement.

A multistage mass spectrometry of an analyte comprises more than one successive mass determining step. A multistage mass spectrometry process involves a) determining the molecular weight (MW) of the analyte as a whole (so-called parent molecule), b) isolating a defined charge state of the parent molecule within the mass spectrometer, c) applying energy to the parent molecule yielding the fragmentation of the analyte into daughter fragments, d) determining the MW of the daughter fragments and e) optionally repeating steps b)-d) for the next mass spectrometric step using a selected daughter fragment produced in step c) for further fragmenting and so on. In case of two mass determining steps (a)-d)), the multistage mass spectrometry is also named tandem—MS or MS/MS. If more than two mass determining steps are performed, the multistage mass spectrometry is identified as $MS^n$ technique.

Note that the determination of the base composition corresponding to the mass of said ionized target nucleic acid in step iii) is only optional and can be avoided in some cases, for example, when the base composition of the target nucleic acids is known already prior to the mass spectrometric analysis.

In general, the fragmentation of the parent molecules in step c) is performed by a collision induced dissociation (CID). This CID fragmentation is achieved by energetically charging the molecules within the collision cell or ion trap of the mass spectrometer via collisions with inert atoms or via resonance activation. The amount of energy provided determines the degree of fragmentation. The entirety of said CID fragments are analyzed afterwards with respect to their mass resulting in the mass spectrum of the CID fragments, a set of experimental peaks representing the CID fragments of the target nucleic acid.

Mass Spectrometry generally involves the ionization of the analyte. In Electrospray-MS, the analyte is initially dissolved in liquid aerosol droplets. Under the influence of high electromagnetic fields and elevated temperature and/or application of a drying gas the droplets get charged and the liquid matrix evaporates. After all liquid matrix is evaporated the charges remain localized at the analyte molecules that are transferred into the Mass Spectrometer. In matrix assisted laser desorption ionization (MALDI) a mixture of analyte and matrix is irradiated by a laser beam. This results in localized ionization of the matrix material and the desorption of analyte and matrix. The ionization of the analyte is believed to happen by charge transfer from the matrix material in the gas phase.

The ionized target nucleic acid is usually generated by negatively charging the phosphate backbone via proton abstraction from the P—O—H groups. This involves running the Mass Spectrometer in negative mode.

A nucleic acid molecule comprises a certain number of 4 different nucleotide bases. Therefore, a nucleic acid molecule with a length of n nucleotide bases can have $4^n$ different base sequences. If the base composition of the nucleic acid molecule is known, e.g. by measuring the molecular mass, the number of possible base sequences of a n-mer is reduced to $n!/(n_A! \cdot n_T! \cdot n_C! \cdot n_G!)$, wherein $n_A$, $n_T$, $n_C$ and $n_G$ are the number of the corresponding bases within the nucleic acid.

The calculated CID mass spectra is obtained by applying the theory of collision induced dissociation for nucleic acids. For a set of nucleic acids the expected fragmentation pattern in the mass spectrum is computed using a set of rules published by Huber et al. (WO 03/025219 A2) and the molecular weight of-each of the expected fragments is translated into a m/z values. The collectivity of all fragment m/z values of one individual nucleic acid represents the calculated CID mass spectrum of said individual nucleic acid, a collectivity of theoretical peaks representing the expected CID fragments of an individual nucleic acid. The calculated CID mass spectra are compared with the measured CID mass spectrum in order to find the closest match between the collectivities of theoretical peaks and the set of experimental peaks.

The comparison of the calculated CID mass spectra with the measured CID mass spectrum is performed by an optimization algorithm. An optimization algorithm comprises a finite set of well-defined instructions for finding the best alternative out of a plurality of possible solutions. These optimization algorithms can be implemented by computer programs. Here, the measured CID mass spectrum is compared with a plurality of calculated CID mass spectra in order to find the closest match between the set of experimental mass peaks of the measured CID mass spectrum and the collectivities of theoretical peaks of the calculated CID mass spectra. The optimization algorithm works successively, wherein one calculated CID mass spectrum is compared with the measured CID mass spectrum after the other. For each of said comparisons a score value is calculated, representing the degree of consistency between said measured CID mass spectrum and the respective calculated CID mass spectrum. Every peak in the measured CID mass spectrum that can be matched with a peak in the respective calculated CID mass spectrum improves said score value. There are mainly two parameters that may be used to define a match between a peak in the measured CID mass spectrum and a peak in the respective calculated CID mass spectrum: the m/z values and the intensities of the peaks. Within the scope of this invention, the calculated CID mass spectrum yielding the best score value is selected as the calculated CID mass spectrum belonging to the base sequence of the target nucleic acid. Throughout the present invention, the best score value is equal to the highest degree of consistency between the measured CID mass spectrum and the calculated CID mass spectra.

Another aspect of the present invention is a program of instructions executable by a computer-implemented system for the sequencing of a target nucleic acid based on the comparison of a measured CID mass spectrum of said target nucleic acid with a plurality of calculated CID mass spectra, wherein the base composition of said target nucleic acid is known and wherein each of said calculated CID mass spectra corresponds to a base sequence having the base composition of said target nucleic acid in order to automatically determine the base sequence of the target nucleic acid
characterized in that said comparison of the measured CID mass spectrum with the calculated CID mass spectra is performed by an optimization algorithm, wherein said optimization algorithm compares said measured CID mass spectrum successively with said plurality of calculated CID mass spectra and determines the respective score value of each comparison, said score value representing the degree of consistency between said measured CID mass spectrum and said calculated CID mass spectra, and wherein the base sequence corresponding to the calculated CID mass spectra yielding the best score value is selected as the base sequence of said target nucleic acid.

The present invention also concerns a computer program product embodying the program of instructions according to the present invention.

Yet another aspect of the invention concerns the use of a computer program product according to the invention for the sequencing of nucleic acids.

Another subject matter of the invention concerns a kit for the de-novo sequencing of nucleic acids according to the present invention comprising a set of dNTPs, a set of NTPs, buffer solutions, an alkaline fragmentation solution and one, two, three or four different engineered polymerases.

The alkaline fragmentation is usually performed using an alkaline fragmentation solution having a pH>9 and can be achieved using e.g. ammonium hydroxide, sodium hydroxide or potassium hydroxide or derivatives thereof in aqueous solution.

Yet another subject matter of the invention is a computer-implemented system to perform the sequencing of nucleic acids according to the present invention comprising a multi-stage mass spectrometer and a program of instructions according to the present invention.

BRIEF DESCRIPTION OF THE DRAWINGS

FIG. 14: Sequences of the forward and reverse single strand primer extension products, wherein primer sequences are underlined. The expected riboA specific fragments together with their MWs are also included. All sequences are written from 5' to 3'. Fragments from the forward strand are marked with 'F', fragments from the reverse strand are marked with 'R'.
FIG. 15: Sequence of the 87 bp ribo-PCR product (SEQ ID NO:2), wherein primer sequences are underlined. A list of fragments after A-specific cleavage of the PCR product is also shown. Fragments from the forward strand are marked with 'F', fragments from the reverse strand are marked with 'R'.

DETAILED DESCRIPTION OF THE INVENTION

Figure 1:
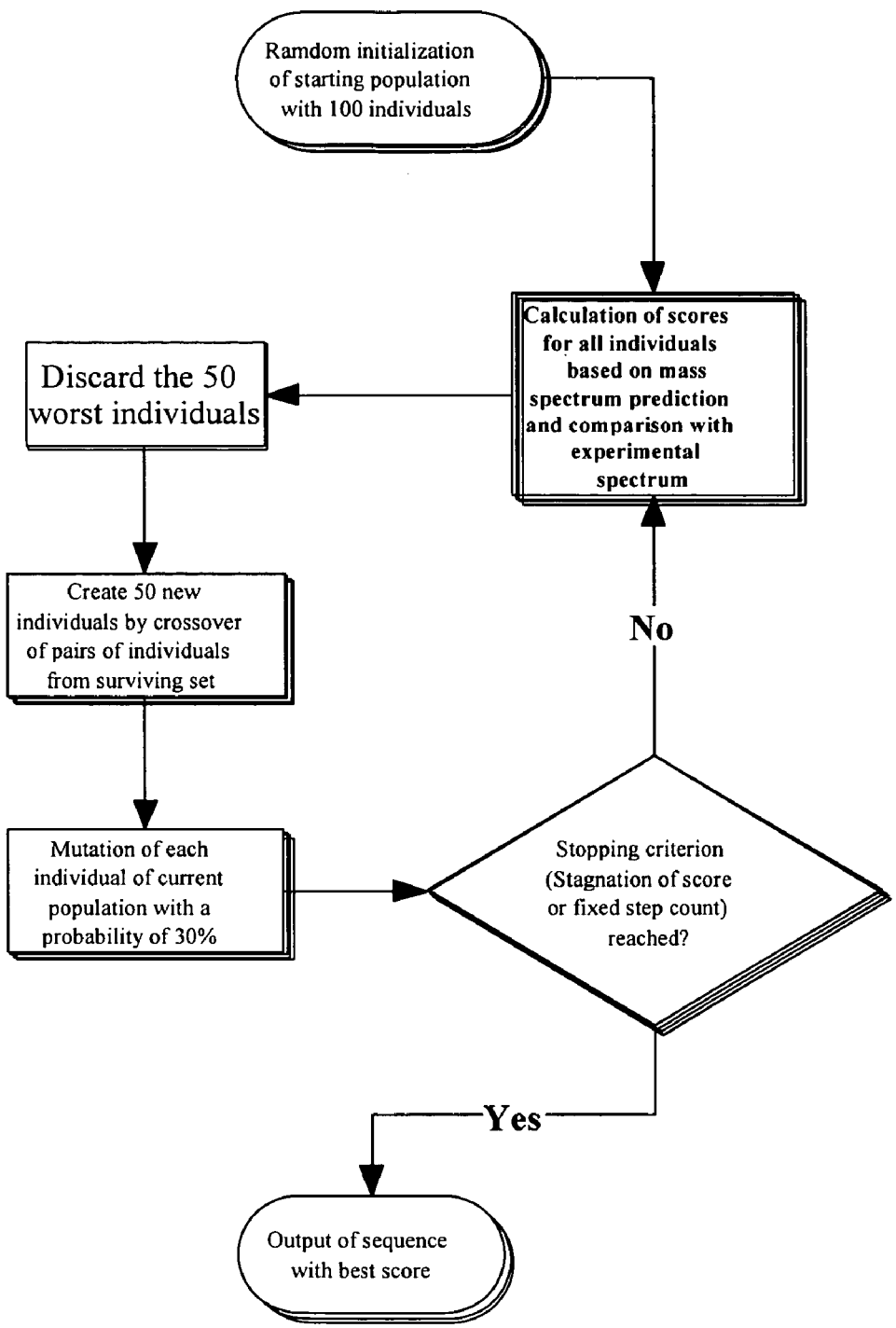
FIG. 1: Schematic diagram of the optimization algorithm.

One subject matter of the present invention is a method for the sequencing of a target nucleic acid comprising:
a) performing a multistage mass spectrometry, comprising
  i) ionizing said target nucleic acid,
  ii) measuring the mass of the ionized target nucleic acid,
  iii) determining the base composition corresponding to the mass of said ionized target nucleic acid,
  iv) fragmenting said ionized target nucleic acid by a collision induced dissociation (CID) and
  v) measuring the corresponding mass spectrum of the CID fragments, and
b) comparing the measured CID mass spectrum of the target nucleic acid measured in step v) with a plurality of calculated CID mass spectra, wherein each of said calculated CID mass spectra correspond to a base sequence having the base composition determined in step iii).

In some embodiments, the method is characterized in that the comparison of the measured CID mass spectrum with the calculated CID mass spectra is performed by an optimization-algorithm. In some embodiments, said optimization algorithm compares said measured CID mass spectrum successively with said plurality of calculated CID mass spectra and determines a respective score value for each comparison, said score value representing the degree of consistency between said measured CID mass spectrum and said calculated CID mass spectra. In some embodiments, the base sequence corresponding to the calculated CID mass spectra yielding the best score value is selected as the base sequence of said target nucleic acid.

In embodiments according to the present invention, said target nucleic acid is amplified prior to performing said multistage mass spectrometry in step a).

In most cases the target nucleic acid is amplified prior to the MS analysis, since the nucleic acid content of e.g. biological samples is usually far below the level of detection. A well-known assay which entails the selective binding of two oligonucleotide primers is the polymerase chain reaction (PCR) described in U.S. Pat. No. 4,683,195. This method allows the selective amplification of a specific nucleic acid region to detectable levels by a thermostable polymerase in the presence of deoxynucleotide triphosphates in several cycles. Other possible amplification reactions are the Ligase Chain Reaction (LCR, Wu D Y and Wallace R B Genomics 4 (1989) 560-569), Polymerase Ligase Chain Reaction (Barany PCR Methods and Applic. 1 (1991) 5-16), Gap-LCR (WO 90/01069), Repair Chain Reaction (EP 439 182 A2), 3SR (Kwoh D. Y. et al. Proc. Natl. Acad. Sci. USA 86 (1989) 1173-1177; WO 92/0880A), and NASBA (U.S. Pat. No. 5,130,238). Further, there are strand displacement amplification (SDA), transcription mediated amplification (TMA), and Qβ-amplification (for a review see e.g. Whelen A C and Persing D H Annu. Rev. Microbiol. 50 (1996) 349-373; Abramson R D and Myers T W Current Opinion in Biotechnology 4 (1993) 41-47).

In an embodiment according to the present invention, said target nucleic acid is amplified prior to performing said multistage mass spectrometry in step a) by a PCR amplification.

One special form of PCR is represented by the single strand primer extension reaction, which is a PCR reaction with only one primer in the amplification solution. In this case a single primer is extended along a template resulting in linear amplification of only one of the two strands. The single primer extension reaction is a special case of an asymmetric PCR amplification, wherein one primer has a concentration of zero. In most cases the template used for single strand primer extension is a PCR product itself.

In another embodiment of the present invention, said target nucleic acid is amplified prior to performing said multistage mass spectrometry in step a) by a single primer extension reaction.

Throughout the present invention the single primer extension reaction may be used as an amplification reaction, because in this case the amplification product comprises only one amplified nucleic acid and therefore, the subsequent fragmentation reaction in step iv) produces a reduced amount of different nucleic acid fragments that have to be evaluated in one mass spectrometric analysis.

In another embodiment of the present invention, said target nucleic acid is separated from other components of the sample prior to performing said multistage mass spectrometry in step a).

In most cases the target nucleic acid is provided in a sample comprising several other components, such as, e.g., salt, other nucleotides, enzymes, organic solvents, detergents and buffer components. This is especially true for target nucleic acids in solution after the amplification by PCR. In some embodiments, the target nucleic acids are separated from said other components of the sample prior to the analysis with mass spectrometry. This separation can be performed e.g. by filtration or specific binding reactions.

In another embodiment of the invention, the separation is performed by liquid chromatography or capillary electrophoresis and said separation is performed in an offline or an online fashion.

In this embodiment of the invention, the separation is performed by capillary electrophoresis or liquid chromatography (LC). Here, the target nucleic acids themselves are also separated by the column depending on their polarity. In general, the less polar and longer the target nucleic acids the slower they will move through the column. These separation techniques can be performed in an offline or an online fashion. Performing the separation technique in an online fashion, the sample is transferred directly to the mass spectrometer after passing the column and the different components of the sample are analyzed as they elute from the column distributed in time. Performing the separation technique in an offline fashion, the sample is initially separated by the column and the different fractions are stored separately for a later analysis.

In yet another embodiment of the present invention the ionization in step i) is an electrospray ionization, a desorption electrospray ionization, a matrix-assisted laser desorption ionization or a fast atom bombardment.

For a detailed description of electrospray ionization (ESI) and matrix-assisted laser desorption ionization (MALDI) see e.g. Mano N et al. Anal. Sciences 19 (1) (2003) 3-14. For a description of desorption electrospray ionization (DESI) see Takats Z et al. Science 306 (5695) (2004) 471-473.

In yet another embodiment of the invention, the multistage mass spectrometry (MS) is performed by ion-trap MS, triple quadrupol MS, time of flight (TOF) MS, quadrupol TOF MS, Fourier transform MS or combinations thereof.

For a detailed description of MS techniques see Mano N et al. Anal. Sciences 19 (1) (2003) 3-14.

In a method according to the present invention, said optimization algorithm is a deterministic algorithm yielding its result by comparing the measured CID mass spectrum with all calculated CID mass spectra that correspond to nucleic acid sequences having the base composition of the target nucleic acid.

Applying a deterministic algorithm for nucleic acid sequencing denotes that all possible sequences corresponding to a known base composition have to be compared to the measured CID mass spectrum of the target nucleic acid. Consequently, the number of necessary comparison steps increases with the number of bases of the target nucleic acid molecule and a deterministic algorithm can reasonably be applied only for short oligonucleotides.

In another embodiment of the invention said optimization algorithm is a stochastic algorithm yielding its result by comparing the measured CID mass spectrum with only a fraction of all calculated CID mass spectra that correspond to nucleic acid sequences having the base composition of the target nucleic acid.

A deterministic algorithm guarantees finding the solution to a given problem, because this algorithm performs all possible evaluation steps, requiring a lot of time. The stochastic algorithm employs an element of chance, which makes the outcome of a single run uncertain. Despite this element of uncertainty, most stochastic optimization techniques are very successful in finding even the global optimum in a large search space. A stochastic optimization algorithm is usually capable of searching larger sets and still finding the right solution in an acceptable amount of time (Fogel D B An introduction to simulated evolutionary optimization, IEEE Transactions on Neural Networks 5 (1994) 3-14).

In yet another embodiment of the present invention, said stochastic algorithm is a simulated annealing algorithm.

A simulated annealing algorithm is a global optimization technique which exploits an analogy between the way in which a liquid compound cools and reorganizes itself into a perfect crystalline state and the search for an optimal solution in a more general optimization problem (Kirkpatrick S; Gerlatt C D J; Vecchi M P Optimization by simulated annealing Science 220 (1983) 671-680).

In an embodiment of the invention said stochastic algorithm reduces the amount of necessary comparison steps by applying a Darwinian evolution analogy comprising aa) choosing a population of parent sequences all having said base composition determined in step iii), bb) selecting a fraction of parent sequences from said population of parent sequences, wherein the selection of said fraction of parent sequences is based on the comparison of score values of the calculated CID mass spectra of said population of parent sequences with respect to said measured CID mass spectrum measured in step v), cc) producing a population of daughter sequences comprising said fraction of parent sequences and altered sequences obtained by recombination of parent sequences from said fraction of parent sequences and dd) repeating steps aa) to cc), wherein said population of daughter sequences produced in step cc) is used as the population of parent sequences for the next evolution step.

Said stochastic algorithm applying a Darwinian evolution analogy belongs to the group of genetic algorithms (Walbridge C T Genetic Algorithms—What Computers Can Learn from Darwin. Technology Review 92 (1989) 46-) and exploits an analogy between Darwinian evolution (survival of the fittest) and a general optimization problem.

Throughout the present invention, the Darwinian algorithm requires some input parameters in order to perform the sequencing of a target nucleic acid based on the measured CID mass spectrum, namely the base composition of target nucleic acid, the charge state of the target nucleic acid used for the CID fragmentation, the measured CID mass spectrum, the size of the population of parent sequences and the comparison delta value. In some embodiments of the Darwinian algorithm according to the present invention the additional parameters mutation probability and crossover window size are desired. All of these parameters are explained in detail in the following.

The base composition of the target nucleic acid can be determined from the set of m/z peaks of the ionized target nucleic acid as obtained in the first step of the multistage mass spectrometry. This first step of the multistage mass spectrometry is performed in so-called full scan mode and the envelope of all differently charged species of one type of ionized target nucleic acid is recorded. The occurrence of the different charge states of said ionized target nucleic acid can be quiet different and the mass spectrometer choose the most abundant charged species for the subsequent fragmentation by CID in the second step of the multistage mass spectrometry. The charge state of the most abundant charged species must be recorded together with the CID mass spectrum, because this parameter is necessary for the subsequent optimization algorithm.

Note that if the base composition of the target nucleic acid is already known prior to said mass spectrometric analysis, the determination of the base composition corresponding to the mass of said ionized target nucleic acid in step iii) is not necessary and therefore, this step of the method is only optional. Nevertheless, the charge of the ionized target nucleic acid that is used for the subsequent fragmentation step of the multistage mass spectrometry must be determined, because it is still necessary for the subsequent optimization algorithm.

The Darwinian algorithm starts by creating a random population of oligonucleotide sequences, which is called the population of parent sequences (generation g=1) in the following. All of these parent sequences share the same base composition ($A_a C_c G_g T_t$, wherein a, c, g, t are the number of the respective base), which has been determined before by inspection of the molecular ion peak of mass spectrometry (step iii) or which is already known prior to said mass spectrometric analysis. Obeying the boundary condition of a given base composition, the population of parent sequences is initialized by generating a certain number of base sequences, wherein for a given composition $A_a C_c G_g T_t$ the bases A, C, G, and T are used a, c, g, and t times, respectively and wherein the placement of each of the bases in the sequence is determined by a random generator.

In the second step, this population of parent sequences is now evaluated by a scoring function: For each of the parent sequences of generation 1, the expected fragmentation pattern of the mass spectrum is computed using a set of rules published by Huber et al. (WO 03/025219 A2) and the molecular weight of each of the expected fragments is translated into m/z values. The collectivity of all m/z values for one parent sequence represents the calculated CID mass spectrum of said parent sequence. The calculated CID mass spectra are compared with the measured CID mass spectrum in order to find the closest match between the collectivities of theoretical peaks and the set of experimental peaks. For each of said comparisons a score value is calculated, representing the degree of consistency between said measured CID mass spectrum and the respective calculated CID mass spectrum. Every peak in the measured CID mass spectrum that can be matched with a peak in the respective calculated CID mass spectrum improves said score value.

There are mainly two parameters that may be used to define a match between a peak in the measured CID mass spectrum and a peak in the respective calculated CID mass spectrum: the m/z values and the intensities of the peaks. In an embodiment according to the invention, a match of peaks is identified, if the m/z value of a peak within a calculated CID mass spectrum is within a certain range of $\Delta(m/z)$ from a peak in the measured CID mass spectrum. The parameter $\Delta(m/z)$ is also called the comparison delta value. Optionally, the match of peaks can be weighted by taking into account the intensities of both the peak of the calculated CID mass spectrum and the peak of the measured CID mass spectrum. If the intensities of the peaks correspond within a defined range, this match is assigned an improved impact to the score value. If the intensities of the peaks do not correspond within a defined range, this match is assigned a declined impact to the score value.

Upon calculation of the score values, a fraction of said population of parent sequences is chosen for the next generation (g+1), the population of daughter sequences, wherein the other fraction of said population of parent sequences is dismissed. The decision, if a certain parent sequence is allowed to moved to the next generation depends on its score value.

Consequently, the size of said fraction of parent sequences is smaller than the size of the initial size of the population of parent sequences. Therefore, in order to have a population of daughter sequences with the same size as said population of parent sequences, the amount of missing sequences are formed by selecting parent sequences from said fraction of parent sequences and creating altered sequences as recombinations thereof.

In an embodiment of the present invention, said population of daughter sequences has the same size as said population of parent sequences.

In another embodiment of the present invention, said recombination of parent sequences to produce said altered sequences in step cc) is performed by exchanging a group of bases between two selected parent sequences of said fraction of parent sequences selected in step bb), wherein said group of bases has the same base composition.

For said recombination of parent sequences, the randomly selected pair of parent sequences exchanges a group of bases within their sequences by performing a so-called crossover: a group of bases within the base sequence of each parent sequence is cut out and exchanged between the parent sequences, wherein the exchanged group of bases must have the same base composition in order to keep the overall base composition unchanged by the crossover process. This is ensured by moving a window of a particular size over the base sequence of both parent sequences, searching for a group of bases that show the same base composition. If such a group of bases is found, the two respective sequence fragments are exchanged to form two altered sequences for the population of daughter sequences.

In another embodiment of the invention, said fraction of parent sequences selected in step bb) comprises between 30% and 80% of said population of parent sequences.

Here, all score values of the parent sequences are compared and a certain fraction yielding the best score values are allowed to move from the population of parent sequences to the population of daughter sequences. The amount of missing sequences in said population of daughter sequences compared with the population of parent sequences of between 70% and 20% is formed by crossover of selected parent sequences as described before.

In an embodiment of the invention, said fraction of parent sequences selected in step bb) comprises 50% of said population of parent sequences.

In this embodiment of the method according to the invention an alternative to the selection of said fraction of parent sequences as explained before is possible. In an embodiment of the present invention, pairs of parent sequences are randomly selected that perform a so-called tournament, where the parent sequence having the better score value wins said tournament. The winner is allowed to move from the population of parent sequences to the population of daughter sequences, wherein the loser is dismissed. Applying this procedure, 50% of the population of parent sequences is moved to the population of daughter sequences.

In another embodiment of the present invention, said group of bases comprises between 10-60%, optionally between 30-50% of the complete parent sequences.

The size of said group of bases can be adjusted relative to the sequence length. If the size of said group of bases becomes too large, the chances to find corresponding groups of bases in the parent sequences are very low and therefore, the crossover can not be performed. Towards smaller sizes of said group of bases, the crossover modification is approaching the sequence modifications by mutation. The crossover modification is used to create a certain amount of changes in the base sequence and therefore, a group of bases comprising only a minor part of the complete parent sequences is not reasonable.

In yet another embodiment of the present invention, a fraction of the daughter sequences of said population of daughter sequences produced in step cc) is altered by mutation prior to the next evolution step, wherein 2 or more bases within one daughter sequence are exchanged.

After filling the population of daughter sequences to the original size of the population of parent sequences by applying crossover, the whole population of daughter sequences may be subjected to an additional mutation step. The mutation of one individual daughter sequence is performed by randomly choosing bases and exchanging their position, wherein the base composition is kept constant. The exchange of bases within one individual daughter sequence can be performed in groups of two or more randomly chosen bases.

In another embodiment of the present invention, 10 to 80%, optionally 20 to 50%, optionally 30 to 40% of said daughter sequences are altered by mutation.

In this embodiment of the invention, the modification of said daughter sequences by mutation is conditional, since it is only applied with a given mutation probability.

In another embodiment according to the present invention, steps aa)-cc) are performed until there is no further improvement of the score values or until a predefined number of repeats is reached.

Once the population of daughter sequences is established, the score values are determined again for all of said daughter sequences as described above, and the process of selecting a fraction of said population of daughter sequences, crossover, optional mutations, and scoring is repeated. In other words, the population of daughter sequences becomes the population of parent sequences of the generation g+1 and the next evolution step is performed. This procedure is repeated until no further improvement of the score values has occurred for a certain number of evolution steps or until a predefined number of evolution steps has been reached.

Finally, the sequence corresponding to the calculated CID mass. spectrum with the best score value is presented to the user as the sequence of the target nucleic acid together with a visual comparison of the calculated and the measured CID mass spectrum and a tabular view of the result. The latter allows the user to judge the validity of the result, since there is a certain probability that the stochastic algorithm provided the wrong base sequence.

In another embodiment of the present invention, if in step iii) more than one base composition is determined to correspond to the mass of said ionized target nucleic acid measured in step ii), the comparison of step b) is performed for each of the determined base composition, the base sequences having the best score value for each of said base compositions are obtained and the base sequence having the best score value of all of said base compositions is selected as the base sequence of said target nucleic acid.

If the molecular ion peak of the target nucleic acid in step iii) can not be assigned to one single base composition, but there are more base compositions able to explain the measured ion peak, the optimization algorithm can be used mainly in two different ways. The first possibility is based on a separate analysis procedure for each of said base compositions. Here, a base sequence corresponding to the calculated CID mass spectrum with the best score value is determined for each of said base compositions and the base sequence having the best score value of all of said base compositions is selected as the base sequence of said target nucleic acid.

In yet another embodiment of the present invention, if in step iii) more than one base composition is determined to correspond to the mass of said ionized target nucleic acid measured in step ii), all of said determined base compositions are used for the comparison in step b).

This second possibility is based on a population of parent sequences that has been chosen from a pool of sequences, wherein said pool of sequences comprises all possible base sequences having one of said base compositions. Afterwards, the optimization algorithm is performed as explained before.

In an embodiment of the invention, the calculated CID mass spectra are obtained using the theoretical fragmentation scheme of collision induced dissociation of nucleic acids.

The theoretical rules for gas phase fragmentation of oligonucleotides by collision induced dissociation are described in Oberacher H et al Anal. Chem. 74 (1) (2002) 211-218 and more recently in Wu J et al Int. J. of Mass Spec. 237 (2-3) (2004) 197-241.

In an embodiment of the invention, the target nucleic acid has a base sequence with a length of not more than 30 bases.

As described before, the number of different base sequences corresponding to a certain base composition becomes very large for long target nucleic acids. Therefore, the probability that the stochastic algorithm provides the wrong base sequence increases with the length of the target nucleic acid. If further information about a certain target nucleic acid is available that helps to reduce the amount of potential base sequences of said target nucleic acid, it is possible to sequence much longer polynucleotides. In this respect, the method of the present invention as described above is applicable for the re-sequencing of long nucleic acids.

In an embodiment of the invention, the target nucleic acid has a base sequence with a length of not more than 15 bases.

In an embodiment of the invention, said sequencing of the target nucleic acid is a de-novo sequencing.

If no further information about a certain target nucleic acid is available and the length of its base sequence is to long to be sequenced directly, the method of the present invention is applicable with an additional fragmentation step prior to the mass spectrometric analysis.

In an embodiment of the present invention for target nucleic acids with a length of more than 30 bases, optionally of more than 15 bases, the method of the present invention comprise the additional step of
a) fragmenting the target nucleic acids into subsequences having a length of not more than 30 bases, optionally of not more than 15 bases wherein step a) is performed prior to performing said multistage mass spectrometry in step a), wherein for each of said subsequences a base composition is determined in step iii) and a CID mass spectrum is measured in step v) and wherein the base sequences corresponding to the calculated CID mass spectra each yielding the best score value for the respective subsequences are the base sequences of said subsequences.

Within the scope of this invention, the fragmentation of nucleic acids comprises all possibilities to split a certain nucleic acid into two or more fragments. The fragmentation can be performed specifically or nonspecifically, by chemical and/or mechanical treatment, by enzymatic cleavage or by controlled termination of the enzymatic replication.

Since nucleic acid fragments of in general less than 3 bases may not be analyzed by mass spectrometry, the fragmentation of nucleic acid according to the present invention should be optimized towards fragments having more than 3 bases.

In an embodiment of the present invention, the fragmentation in step a0) produces nucleic acid fragments with more than 3 bases.

In an embodiment of the present invention, the fragmentation in step a0) is performed by enzymatic digestion.

In an embodiment of the present invention, said enzymatic digestion is performed using an enzyme of the RNASeIII family, e.g., a Dicer enzyme or restriction enzymes, e.g., a 4-cutter enzyme.

The Dicer enzymes are usually used to generate siRNAs for gene silencing experiments and cut dsRNA into pieces of about 19-22 bp. Restriction endonucleases recognize a specific DNA base sequence and cut within or nearby this region. The shorter the length of the recognition sequence the higher is the probability for cleavage.

In an embodiment of the present invention, an amplification reaction of said target nucleic acid is performed prior to the fragmentation in step a0), wherein said amplification reaction is performed with deoxyribonucleotides (dNTP), ribonucleotides (NTP) and an engineered polymerase having the ability to incorporate both dNTPs and NTPs and wherein said fragmentation in step a0) is performed by an alkaline hydrolysis.

Standard polymerases that are widely used for PCR amplifications in general do not comprise the ability to incorporate NTPs into the amplification product. Therefore, nucleic acids comprising both dNTPs and NTPs are not obtainable with standard polymerases.

However, there are engineered polymerases known in the art having a reduced discrimination against NTPs (Gelfand et al, U.S. Pat. No. 5,939,292). After an amplification step with said engineered polymerase, wherein both dNTPs and NTPs are provided in the amplification solution, the amplification product comprises a mixture of dNTPs and NTPs. These mixed nucleic acids provide the opportunity to use a simple alkaline hydrolysis step for the controlled fragmentation at the NTP base positions of the amplicon. Ribonucleotides contain a 2'-OH group that under alkaline conditions form a cyclic intermediate. Formation of this cyclic intermediate results in cleavage of the nucleic acid. Said alkaline fragmentation is usually performed using an alkaline fragmentation solution having a pH>9 and can be achieved using e.g. ammonium hydroxide, sodium hydroxide or potassium hydroxide or derivatives thereof in aqueous solution.

In another embodiment according to the present invention, the base sequences of said subsequences are used to reconstruct the base sequence of said target nucleic acid.

In this embodiment according to the present invention, the knowledge of the base sequences of all subsequences produced by the fragmentation in step a0) is used to reconstruct the base sequence of the target nucleic acid. Depending on the fragmentation procedure, this knowledge is sufficient to perform a re-sequencing or a de-novo sequencing of the target nucleic acid.

In an embodiment of the present invention, the sequencing of the target nucleic acid is a de-novo sequencing of said target nucleic acid comprising
aaa) performing at least two different amplification reactions of said target nucleic acid, wherein in each of said different amplification reactions one of the 4 dNTPs is replaced by the corresponding NTP,
bbb) analyzing each of the different amplification products of said at least two different amplification reactions separately, wherein each of said different amplification products is fragmented by an alkaline hydrolysis step prior to the multistage mass spectrometry and ccc) using the base sequences of all subsequences obtained by the analysis of the different fragmented amplification products to reconstruct the base sequence of the target nucleic acid.

Throughout the present invention the engineered polymerases are used to produce nucleic acids having one of the dNTPs completely replaced by the corresponding NTP. This implicates that the amplification solution for the PCR does not contain the DNTP equivalent of the NTP base to be incorporated.

In an embodiment of the present invention, 100% of the respective dNTP of each of said at least two different amplification reactions is replaced by the corresponding NTP.

The complete replacement of one of the dNTPs results in a reduction of the possible fragments that are produced in the subsequent fragmentation step.

In order to realize a de-novo sequencing of long target nucleic acids based on the controlled fragmentation into subsequences, it is necessary to ensure a sufficient overlap of de-novo sequenced subsequences of said at least two different amplification reactions. Only a sufficient overlap of said subsequences of the at least two fragmentation reactions enables the correct reconstruction of the target nucleic acid base sequence.

In addition, in some embodiments, the complete sequence of the target nucleic acid is covered by the plurality of de-novo sequenced subsequences. Since nucleic acid fragments of in general less than 3 bases may not be analyzed by mass spectrometry, a part of the target nucleic acid base sequence may be lost in each of said at least two fragmentation reactions. In the following, this fact is described by the so-called sequence coverage that should be close to 100% for the correct reconstruction of the target nucleic acid base sequence. Combining the information of said at least two different fragmentation reactions results in an increased sequence coverage.

As an alternative to the reconstruction based on the information from two or more different fragmentation reactions, it is possible to perform the de-novo sequencing of target nucleic acid based on the additional information of the corresponding anti sense strand. Due to the Watson-Crick rules, it is possible to combine information of both strands for the reconstruction of the target nucleic acid base sequence.

In some embodiments of the present invention, three or four different amplification reactions are performed.

If three or even four different amplification reactions are performed, wherein for each of said different amplification reactions another dNTP is replaced by the corresponding NTP, a huge amount of subsequence information is generated providing enough overlap of de-novo sequenced subsequences and sufficient sequence coverage to ensure a precise reconstruction of the base sequence of the target nucleic acid.

In another embodiment of the present invention, more than one different engineered polymerases are used.

In yet another embodiment of the present invention, for each of said different amplification reactions a different engineered polymerase is used.

Within the scope of this invention the different amplification reactions are performed with one or more engineered polymerases. For example, it is possible to provide an engineered polymerase having the ability to incorporate two of the NTP bases and therefore, the at least two different amplification reactions necessary for the method according to the present invention can be performed with one engineered polymerase. Additionally, if more than two different amplification reactions are desired, it is possible to provide an engineered polymerase having the ability to incorporate three or even all four of the NTP bases. On the other hand, it is possible to provide two, three or four different engineered polymerase each having the ability to incorporate one of the NTP bases. In this case, each different amplification reaction is performed with a different engineered polymerase. It is clear to someone skilled in the art that any combination of polymerases are applicable within the scope of this invention.

In an embodiment of the present invention, said multistage mass spectrometry is a tandem mass spectrometry.

A tandem mass spectrometry process involves a) determining the molecular weight (MW) of the target nucleic acid as a whole, b) isolating a defined charge state of the target nucleic acid within the mass spectrometer, c) applying energy to the target nucleic acid resulting in the fragmentation of the target nucleic acid into fragments, and d) determining the MWs of all fragments.

Another aspect of the present invention is a program of instructions executable by a computer-implemented system for the sequencing of a target nucleic acid based on the comparison of a measured CID mass spectrum of said target nucleic acid with a plurality of calculated CID mass spectra, wherein the base composition of said target nucleic acid is known and wherein each of said calculated CID mass spectra corresponds to a base sequence having the base composition of said target nucleic acid in order to automatically determine the base sequence of the target nucleic acid characterized in that said comparison of the measured CID mass spectrum with the calculated CID mass spectra is performed by an optimization algorithm, wherein said optimization algorithm compares said measured CID mass spectrum successively with said plurality of calculated CID mass spectra and determines the respective score value of each comparison, said score value representing the degree of consistency between said measured CID mass spectrum and said calculated CID mass spectra, and wherein the base sequence corresponding to the calculated CID mass spectra yielding the best score value is selected as the base sequence of said target nucleic acid.

The computer-implemented system for the sequencing of a target nucleic acid able to execute said program of instructions according to the invention comprises a computer with an interface for the data input from a multistage mass spectrometer and a visualization device to present the result of said program of instructions to the user. Said program of instructions automatically presents a base sequence for the target nucleic acid under investigation to the user, if certain parameters are provided as input parameters. The base sequence is presented to the user together with a visual comparison of the calculated and the measured CID mass spectrum and a tabular view of the result. The latter allows the user to judge the validity of the result, since there is a certain probability that the program of instructions based on stochastic principals provided the wrong base sequence.

In some programs of instructions according to the present invention, said optimization algorithm is a deterministic algorithm yielding its result by comparing the measured CID mass spectrum with all calculated CID mass spectra that correspond to nucleic acid sequences having the base composition of the target nucleic acid.

In some programs of instructions according to the present invention, said optimization algorithm is a stochastic algorithm yielding its result by comparing the measured CID mass spectrum with only a fraction of all calculated CID mass spectra that correspond to nucleic acid sequences having the base composition of the target nucleic acid.

In some programs of instructions according to the present invention, said stochastic algorithm is a simulated annealing algorithm.

In some programs of instructions according to the present invention, said stochastic algorithm reduces the amount of necessary comparison steps by applying a Darwinian evolution analogy comprising
a) choosing a population of parent sequences having the base composition of said target nucleic acid,
b) selecting a fraction of parent sequences from said population of parent sequences, wherein the selection of said fraction of parent sequences is based on the comparison of score values of the calculated CID mass spectra of said population of parent sequences with respect to said measured CID mass spectrum,
c) producing a population of daughter sequences comprising said fraction of parent sequences and altered sequences obtained by recombination of parent sequences from said fraction of parent sequences and
d) repeating steps a) to c), wherein said population of daughter sequences produced in step c) is used as the population of parent sequences for the next evolution step.

Details about the different algorithms that are applicable for the program of instruction within the scope of the present invention have been reviewed before. In case of the Darwinian algorithm according to the present invention, the optimization algorithm needs the following input parameters in order to automatically present the base sequence of the target nucleic acid to the user, namely the measured CID mass spectrum, the base composition of said target nucleic acid, the charge state of the target nucleic acid used for the CID fragmentation, the size of the population of parent sequences and the comparison delta value. In some embodiments of the Darwinian algorithm according to the present invention, the additional parameters mutation probability and crossover window size are desired.

In some embodiments of the program of instructions according to the invention, said fraction of parent sequences selected in step b) comprises between 30% and 80% of said population of parent sequences.

In some embodiments of the program of instructions according to the invention, said fraction of parent sequences selected in step b) comprises 50% of said population of parent sequences.

The different alternatives of selecting said fraction of parent sequences for the said population of daughter sequences has been reviewed before in the context of the method for the sequencing of a target nucleic acid according to the present invention.

In some embodiments of the program of instructions according to the invention, said population of daughter sequences has the same size as said population of parent sequences.

In some embodiments of the program of instructions according to the invention, said recombination of parent sequences to produce said altered sequences in step c) is performed by exchanging a group of bases between two selected parent sequences of said fraction of parent sequences selected in step b), wherein said group of bases has the same base composition.

In some embodiments of the program of instructions according to the invention, said group of bases comprises between 10-60%, optionally between 30-50% of the complete parent sequences.

The different alternatives of producing altered sequences for the said population of daughter sequences has been reviewed before in the context of the method for the sequencing of a target nucleic acid according to the present invention.

In some programs of instructions according to the present invention, a fraction of the daughter sequences of said population of daughter sequences produced in step c) is altered by mutation prior to the next evolution step, wherein 2 or more bases within one daughter sequence are exchanged.

In some programs of instructions according to the present invention, 10-80%, optionally 20-50%, optionally 30-40% of said daughter sequences are altered by mutation.

The different alternatives for the mutation of sequences of said population of daughter sequences has been reviewed before in the context of the method for the sequencing of a target nucleic acid according to the present invention.

In some programs of instructions according to the present invention, steps a)-c) are performed until there is no further improvement of the score values or until a predefined number of repeats is reached.

In some programs of instructions according to the present invention, the calculated CID mass spectra are obtained using the theoretical fragmentation scheme of collision induced dissociation of nucleic acids.

The theoretical rules for gas phase fragmentation of oligonucleotides by collision induced dissociation are described in Oberacher H et al Anal. Chem. 74 (1) (2002) 211-218 and more recently in Wu J et al Int. J. of Mass Spec. 237 (2-3) (2004) 197-241.

In some embodiments of the program of instructions according to the invention, said sequencing of the target nucleic acid is a de-novo sequencing.

Another aspect of the present invention is a computer program product embodying the program of instructions according to the invention.

Throughout the present invention said computer program product summarizes all computer-readable mediums known to someone skilled in the art.

Yet another aspect of the present invention is the use of a computer program product according to the invention for the sequencing of nucleic acids.

In some uses according to the invention, said sequencing of the target nucleic acid is a de-novo sequencing.

Another subject matter of the present invention is a kit for the sequencing of a target nucleic acid according to the invention comprising a set of dNTPs, a set of NTPs, buffer solutions, an alkaline fragmentation solution and one, two, three, four or more different engineered polymerases.

The alkaline fragmentation is usually performed using an alkaline fragmentation solution having a pH >9 and can be achieved using e.g. ammonium hydroxide, sodium hydroxide or potassium hydroxide or derivatives thereof in aqueous solution. Ribonucleotides contain a 2'-OH group that under alkaline conditions form a cyclic intermediate. Formation of this cyclic intermediate results in cleavage of the nucleic acids.

Yet another subject matter of the present invention is a computer-implemented system to perform the sequencing of nucleic acids according to the invention comprising a multi-stage mass spectrometer and a program of instructions according to the invention.

In some computer-implemented systems according to the invention, said sequencing of the target nucleic acid is a de-novo sequencing.

The following examples, references, sequence listing and figures are provided to aid the understanding of the present invention, the true scope of which is set forth in the appended claims. It is understood that modifications can be made in the procedures set forth without departing from the spirit of the invention.

EXAMPLE 1

Oligonucleotide Sequence Determination Via MS/MS and Computerized Data Analysis

A synthetic 14-mer oligonucleotide (5'-GAGACTGC-CAAGCG-3'; SEQ ID NO:1) was dissolved at a concentration of 5 µM in a solution of 25 mM butyl-dimethyl-ammoniumbicarbonate (BDMAB) in acetonitrile/water (30:70, v/v). The solution was analyzed by electrospray-mass spectrometry on a ThermoElectron LTQ Ion Trap MS instrument using direct infusion at 2 µl/min, wherein the mass spectrometer was run in negative ion mode. In order to obtain optimal analysis conditions, the mass spectrometer was tuned using a 24-mer oligodesoxythymidin ($dT_{24}$) and a mixture of Ultramark, caffeine and MRFA (Thermo Electron Corp., San Jose, Calif.) was used for mass calibration. A voltage of −3.0 kV was employed for the electrospray ionization and the temperature of the transfer capillary was set to 200° C.

Figures 2, 3:
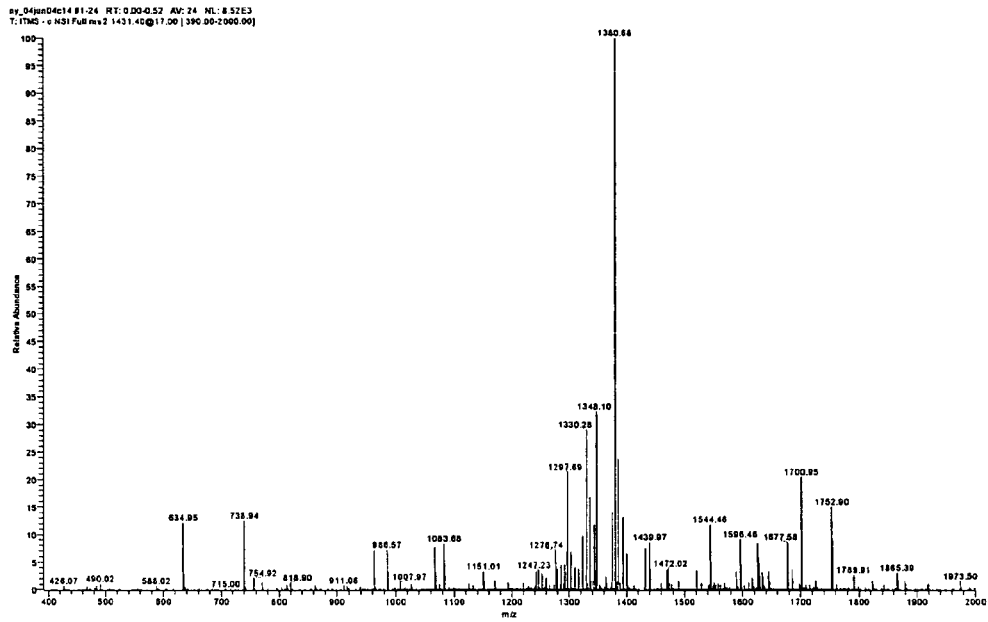
FIG. 2: MS/MS spectrum of 5'-GAGACTGCCAAGCG-3' (SEQ ID NO:1), recorded on a LTQ-Ion Trap MS by direct infusion of a 5 µM solution.
FIG. 3: List of oligonucleotides used for the preparation of the test mixture of Example 2. The molecular weights for monoisotopic (MW mono) and average mass (MW av) resolution together with the corresponding m/z=−2 values are also included.

First, the LTQ was run in full scan mode and the envelope of multiply charged molecular ions was recorded. Afterwards, the most abundant ion at m/z=1431.4 Da corresponding to the oligonucleotide with a charge state of −3 was isolated and fragmented in $MS^2$ mode applying a collision energy of 17%. The resulting fragment ion spectrum (see FIG. 2) was recorded and saved as a text file to be analyzed by the optimization algorithm.

The optimization algorithm as schematically presented in FIG. 1 was executed on a Compaq Evo610c standard laptop computer. Besides the measured fragment ion spectrum other input parameters were the charge state of parent ion and the base composition of the oligonucleotide. The parameters of the used genetic optimization algorithm were set to: Population size: 100; Mutation probability: 30% ; Crossover window size: 40% ; Comparison Delta value: 0.5 Da.

The runtime of the genetic optimization algorithm was around 20 s until the correct sequence was presented. Using this data set, the algorithm was performed more than 50 times and always presented the correct base sequence of the oligonucleotide.

EXAMPLE 2

Sequencing of Oligonucleotides in Mixtures

Eight synthetic oligonucleotides (see FIG. 3) were mixed and dissolved in water at a concentration of 500 nM each. 500 nL of the mixture was separated by High Performance Liquid Chromatography (HPLC) and analyzed by Tandem-Mass Spectrometry in an online fashion. A commercially available computer controlled integrated HPLC system was used (model Surveyor, Thermo Electron Corp., San Jose, Calif.). The system consisted of a gradient micro pump, an autosampler and a microinjector valve with a 500 nL internal sample loop. The 50×0.2 mm i.d. monolithic capillary column was from LC-Packings (Sunnyvale, Calif.).

A flow-rate of 2.0 µL/min through the column was split from a primary flow of 250 µL/min by means of a T-piece and a fused silica restriction capillary. A binary eluent system was used with eluent A (10 mM BDMAB) in water (pH 9) and B (10 mM BDMAB) in water/acetonitrile (40:60) pH 9. The gradient for separation of the oligonucleotide mixture was 100% A (0-5 min), 100%→20% A (5-15 min) and 20% A (15-20 min). The HPLC column was directly connected to the electrospray capillary (fused silica, 90 µm o.d., 20 µm i.d., Polymicro Technologies, Phoenix, Ariz.).

ESI-MS was performed on an ion trap mass spectrometer (LCQ Deca XP, Thermo Electron Corp., San Jose, Calif.) equipped with an electrospray ion source. A voltage of −3.0 kV was employed for the electrospray ionization and the temperature of the transfer capillary was set to 200° C. Total ion chromatograms and mass spectra were recorded on a personal computer with the data analysis software Xcalibur version 1.3 (Thermo Electron). Mass calibration and coarse tuning were performed using a mixture of Ultramark, caffeine and MRFA (Thermo Electron Corp., San Jose, Calif.). Fine tuning for ESI-MS of oligodeoxynucleotides in the negative ion mode was performed with a 24-mer oligodesoxythymidin ($dT_{24}$).

Figure 4:
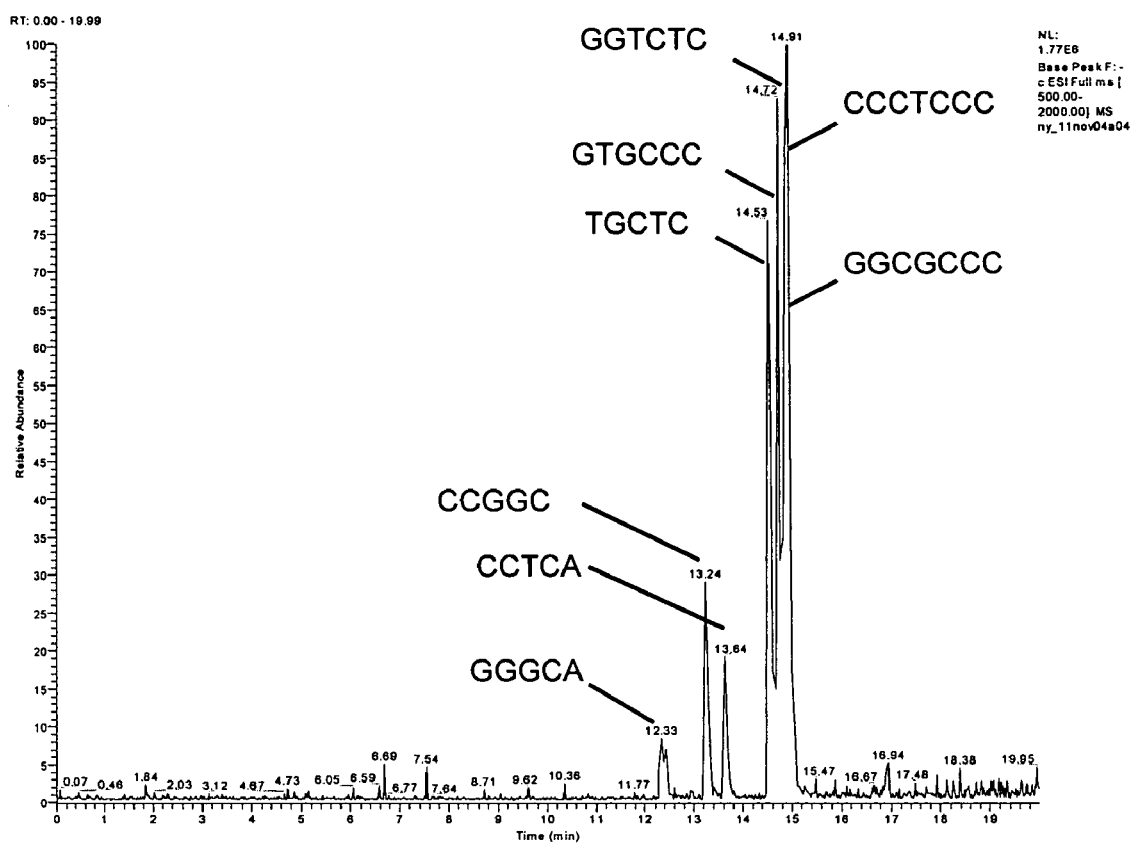
FIG. 4: Base peak chromatogram of the 8-component test mixture recorded on a LCQ Deca XP Mass Spectrometer.
Figure 5:
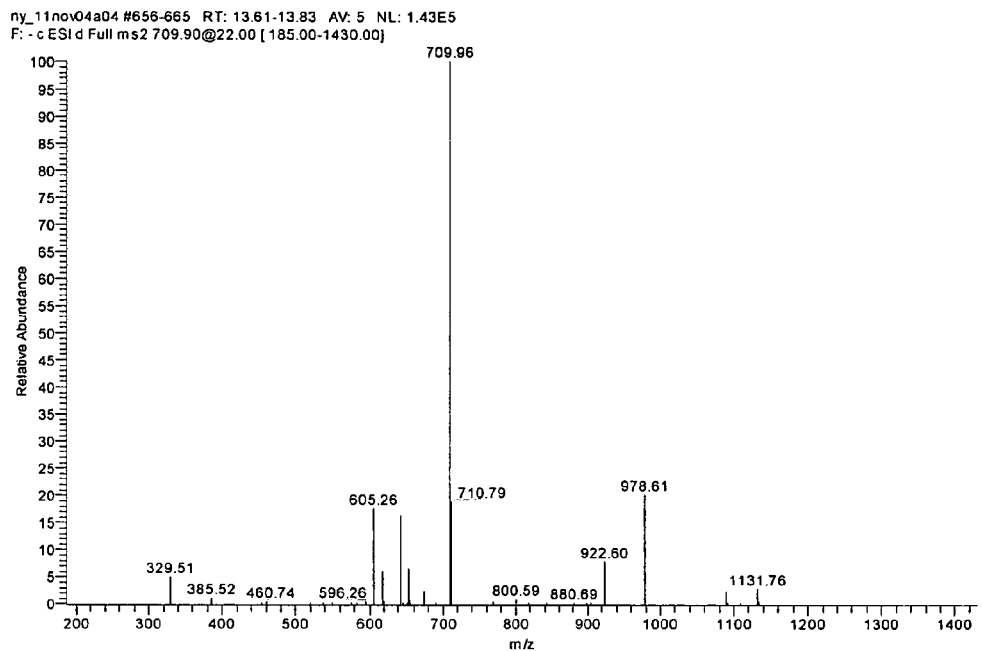
FIG. 5: MS/MS data of 5'-CCTCA-3' used for computerized sequence analysis.
Figure 6:
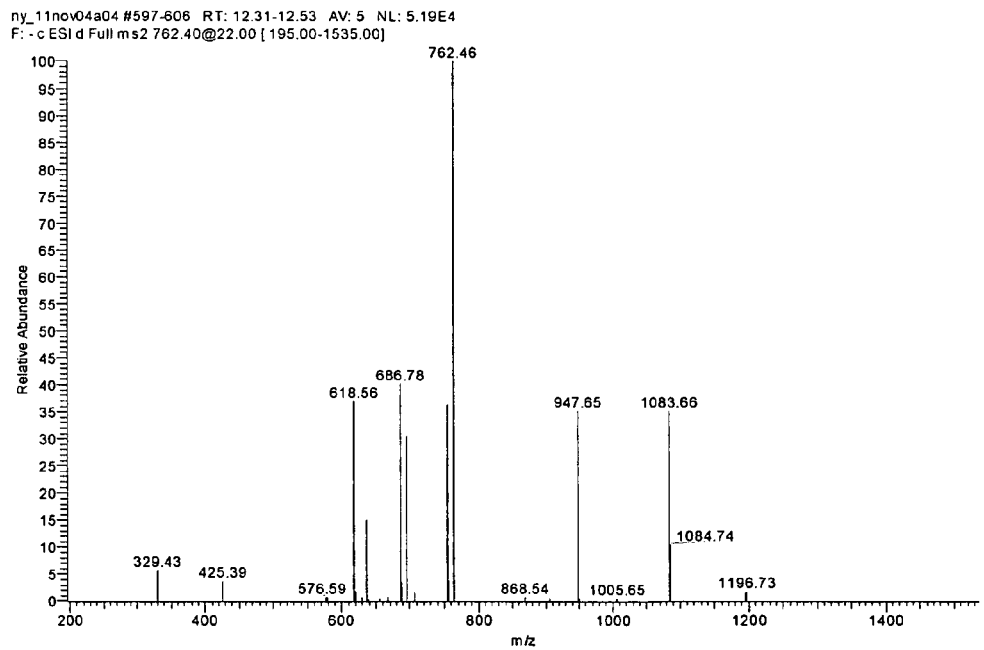
FIG. 6: MS/MS data of 5'-GGGCA-3' used for computerized sequence analysis.
Figure 7:
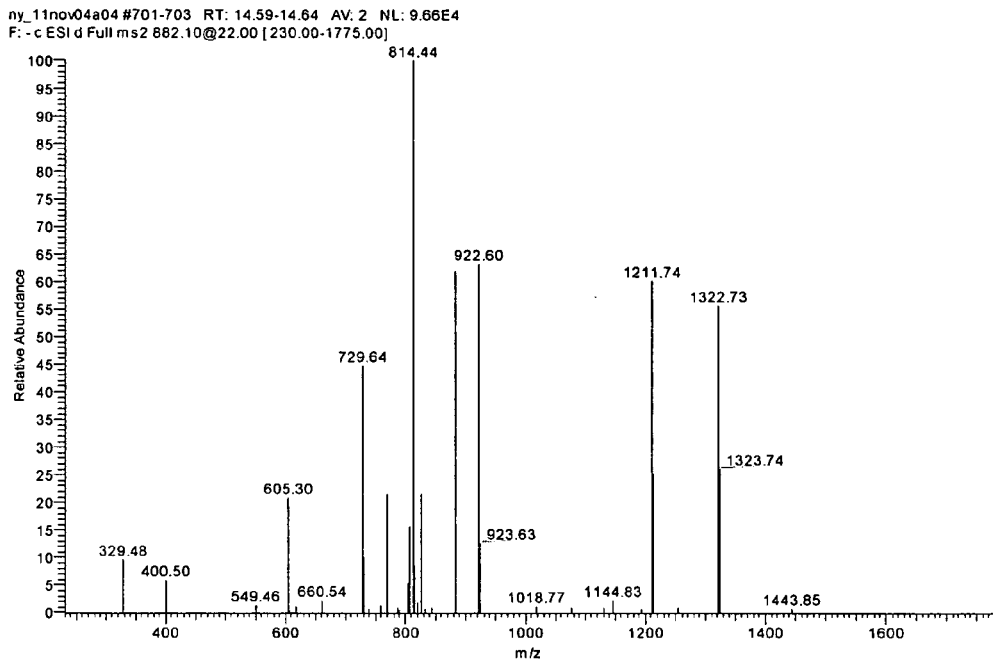
FIG. 7: MS/MS data of 5'-TGCTCA-3' used for computerized sequence analysis.
Figure 8:
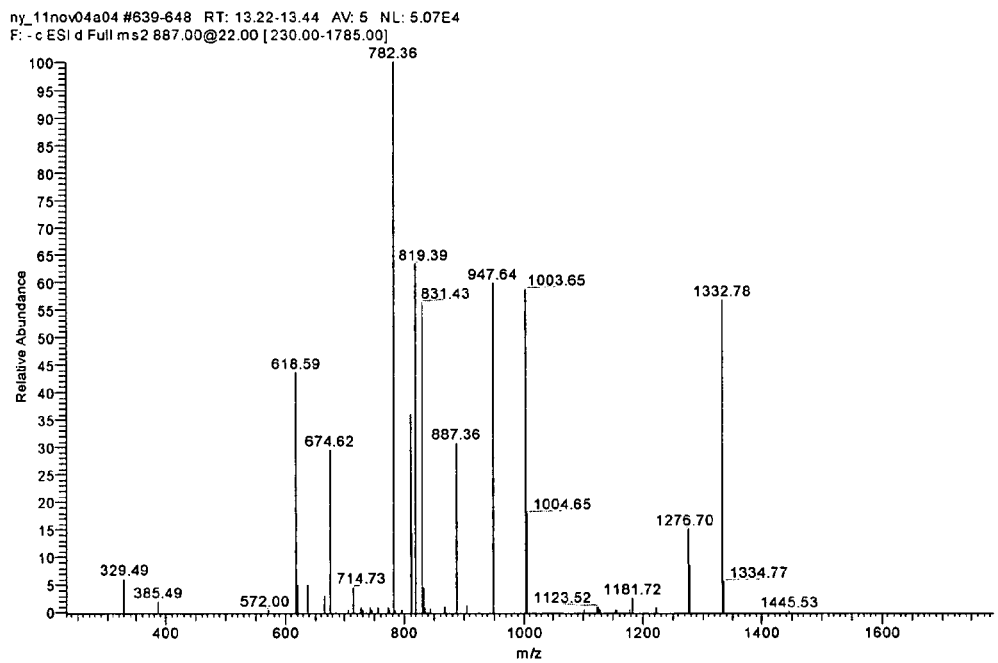
FIG. 8: MS/MS data of 5'-CCGGCA-3' used for computerized sequence analysis.
Figure 9:
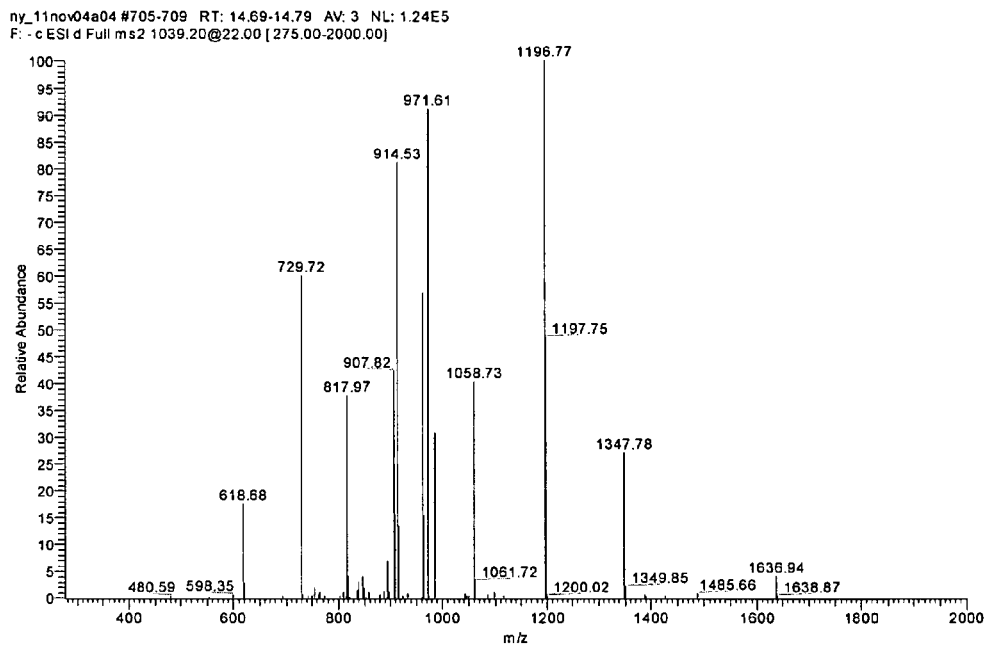
FIG. 9: MS/MS data of 5'-GTGCCCA-3' used for computerized sequence analysis.
Figure 10:
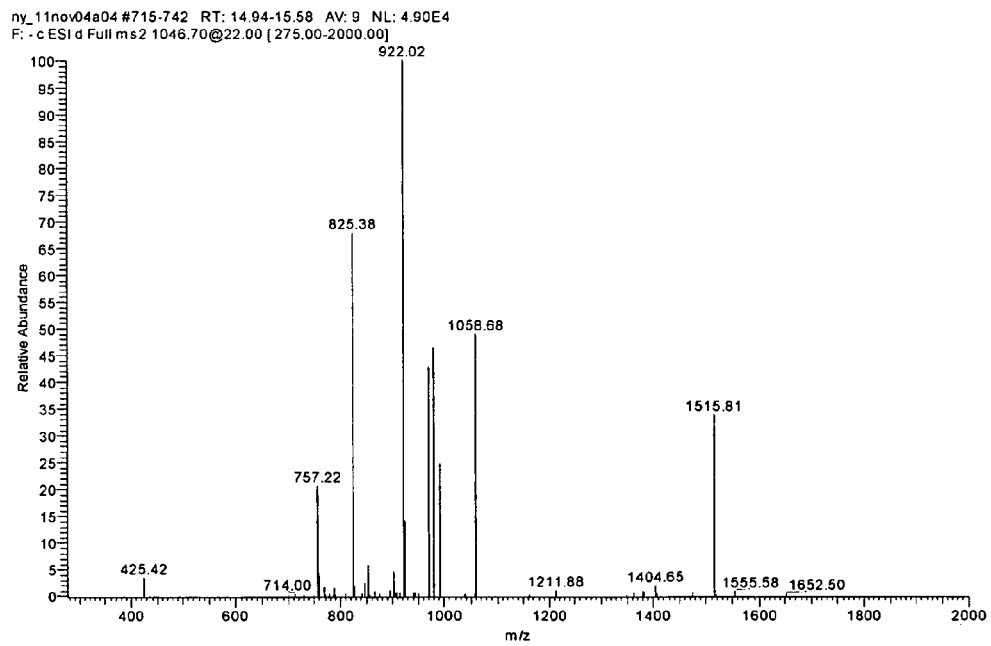
FIG. 10: MS/MS data of 5'-GGTCTCA-3' used for computerized sequence analysis.
Figure 11:
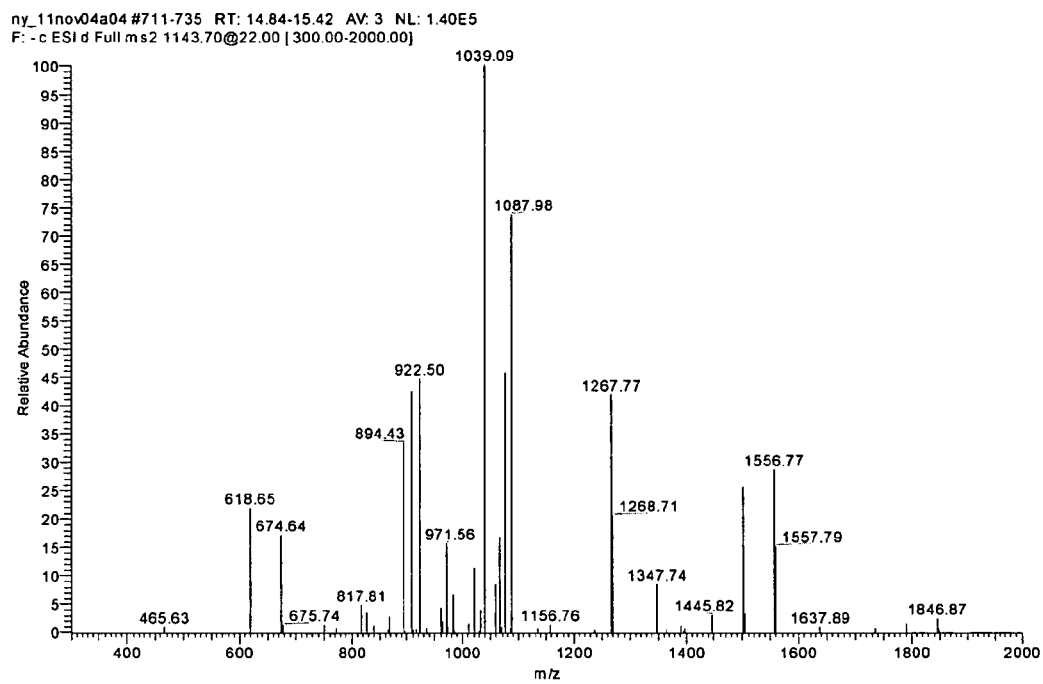
FIG. 11: MS/MS data of 5'-CCCTCCCA-3' used for computerized sequence analysis.
Figures 12, 13:
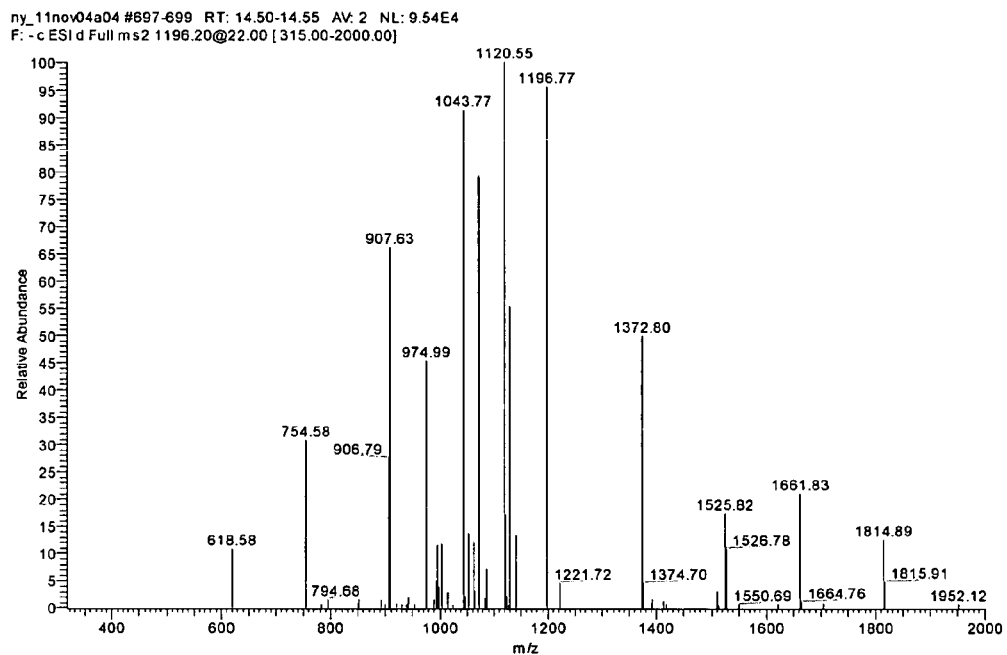
FIG. 12: MS/MS data of 5'-GGCGCCCA-3' used for computerized sequence analysis.
FIG. 13: Sequence of the initial PCR product (SEQ ID NO:2) used as a template for ribo-primer extension reaction. Primer sequences (SEQ ID NO:3 and SEQ ID NO:4) are underlined.

Using this experimental set-up, the molecular weight of all 8 oligonucleotides in the mixture was determined. In order to acquire MS/MS data from the most intense charge state (in this case: m/z=−2) of the oligonucleotides in the mixture, the data dependent scan mode was used. Said data dependent scan mode searches for the most abundant parent ion of every analyte that is than isolated and subsequently fragmented in the ion trap using a collision energy setting of 22%. The fragment ion spectra were recorded and subjected to the computerized sequence analysis. The base peak chromatogram can be found in FIG. 4, whereas the MS/MS spectra of each of the eight synthetic oligonucleotides is plotted in FIGS. 5-12. Not all oligonucleotides of the chromatogram in FIG. 4 could be baseline separated. However, this problem is irrelevant due to the second dimension of separation in the Mass Spectrometry.

The genetic optimization algorithm as schematicallypresented in FIG. 1 was executed on a Compaq Evo610c standard laptop computer. For every oligonucleotide within the mixture MS/MS data, charge state of parent ion and most probable base composition as predicted from the full scan experiment were provided as input parameters for the optimization algorithm. The parameters of the underlying genetic algorithm were set to: Population size: 100; Mutation probability: 30% ; Cross Over window size: 40%; Comparison Delta value: 0.5 Da.

As a result every oligonucleotide within the mixture was sequenced correctly, whereas the runtime of the genetic optimization algorithm was about 20 s for each component of the mixture. The sample-to-sequence time was about 18 min (15 min for HPLC-MS/MS and 3 min algorithm runtime).

EXAMPLE 3

Hydrolytic Cleavage of DNA/RNA Chimers Generated by Single Strand Primer Extension Reactions Followed by MS/MS Analysis of Fragments and Computational Sequence Analysis Two primer extension reactions are performed using an 87 bp PCR (SEQ ID NO:2) product as a template. For both-reactions a specially-engineered DNA polymerase (CS6R DNA polymerase (4 U/µl), obtained by directed evolution; Roche Molecular Systems, Inc.) capable of incorporating riboATPs and riboGTPs is used. The first reaction produces a single stranded extension product with all dAs replaced by riboAs. The second reaction results in the same product corresponding to the reverse strand of the initial PCR product (see FIG. 13 for sequences).

Protocol for Extension Reaction and Hydrolytic Cleavage:

For a final volume of 10 µl: 0.25 µl of CS6R DNA polymerase (4 U/µl), 1 µl of dCTP, dTTP, dGTP, and ATP (4 mM each), 0.5 µl of 200 mM Tris/HCl pH 8.3, 0.5 µl of 500 mM NH₄Cl, 0.5 µl of 50 mM MgCl₂, 0.25 µl of extension primer (40 pmol/µl ; SEQ ID NO:3 or SEQ ID NO:4) and 2 µl of water. The thermal cycling profile for the extension reaction is 2 min at 95° C. followed by 40 cycles of 15 s at 95° C., 2 min at 60° C. and 20 s at 72° C. with a final extension of 4 min at 72° C. After extension, 4.3 µL of 1 M Potassiumhydroxide (KOH) or 1 M Sodiumhydroxide (NaOH) are added to the mixture and incubated at 70° C. for 1.5 hours resulting in hydrolytic cleavage of the NA strands at every incorporated ATP position. The list of fragments can be found in FIG. 14.

The analysis of the fragment mixture is performed as described in example 2: The mixture of cleavage products is directly analyzed by HPLC-ESI-MS/MS and the molecular weights (MW) of all fragments are determined in full scan mode. Optionally, the mixtures can be adjusted to pH=7 and/or desalted prior to MS analysis. The performed MS/MS scan provides CID (collision induced dissociation) fragment data of all cleavage products having a length of more than 3 bases. This data, together with the corresponding base compositions as determined from the MW of each fragment is subjected to computational sequence analysis and the base sequences of all fragments are obtained.

The entire workflow as described above is repeated, but this time for the extension reactions riboGTP is used instead of dGTP and dATP is used instead of riboATP. Therefore, the alkaline hydrolysis results in G-specific cleavage products. The base sequences of this fragments are obtained by computational analysis of their MS/MS data.

Together with the previously obtained sequences from the A-specific cleavage reaction and the information from the corresponding antisense strand the base sequence of the initial 87 bp PCR (SEQ ID NO:2) product can be reconstructed. Optionally, the entire workflow can be performed by additionally replacing dTTP with TTP or dCTP with CTP using an appropriate polymerase.

EXAMPLE 4

Hydrolytic Cleavage of DNA/RNA Chimers Generated by riboPCR Reactions Followed by MS/MS Analysis of Fragments and Computational Sequence Analysis A PCR reaction is performed using an 87 bp PCR (SEQ ID NO:2) product or the appropriate genomic DNA as a template. For the reaction a specially engineered DNA polymerase (CS6R DNA polymerase (4 U/µl), obtained by directed evolution) capable of incorporating riboATPs and riboGTPs is used. The reaction produces a double stranded PCR product with all dAs replaced by riboAs (see FIG. 15 for the sequences).

Protocol for the riboPCR and hydrolytic cleavage:

For a final volume of 10 µl: 0.25 µl of CS6R DNA polymerase (4U/µl), 1 µl of dCTP, dTTP, dGTP, and ATP (4 mM each), 0.5 µl of 200 mM Tris/HCl pH 8.3, 0.5 µl of 500 mM NH₄Cl, 0.5 µl of 50 mM MgCl₂, 0.25 µl of each primer (40 pmol/µl, SEQ ID NO:3 and SEQ ID NO:4) and 1.75 µl of water. The thermal cycling profile is 2 min at 95° C. followed by 40 cycles of 15 s at 95° C., 2 min at 60° C. 72° C. with a final extension of 4 min at 72° C. After the reaction, 4.3 µL of 1 M Potassiumhydroxide (KOH) or 1 M Sodiumhydroxide (NaOH) are added to the mixture and incubated at 70° C. for 1.5 hours resulting in hydrolytic cleavage of the NA strands at every incorporated ATP position. The list of fragments can be found in FIG. 15.

The analysis of the fragment mixture is performed as described in example 2: The mixture of cleavage products is directly analyzed by HPLC-ESI-MS/MS and the MW of all fragments determined in full scan mode. Optionally, the mixtures can be adjusted to pH=7 and/or desalted prior to MS analysis. The performed MS/MS scan provides CID fragment data of all cleavage products having a length of more than 3 bases. This data, together with the corresponding base compositions as determined from the MW of each fragment is subjected to computational sequence analysis and the sequences of all fragments are obtained.

The entire-workflow as described above is repeated, but this time for the PCR reactions riboGTP is used instead of dGTP and dATP is used instead of riboATP. Therefore, the alkaline hydrolysis results in G-specific cleavage products. The sequences of this fragments are obtained by computational analysis of their MS/MS data.

Together with the previously obtained sequences from the A-specific cleavage reaction and the information from the corresponding antisense strand the sequence of the initial 87 bp PCR (SEQ ID NO:2) product can be reconstructed. Optionally, the entire workflow can be performed by additionally replacing dTTP with TTP or dCTP with CTP using an appropriate polymerase.

Various embodiments of the invention have been described. The descriptions and examples are intended to be illustrative of the invention rather than limiting. Indeed, it will be apparent to those of skill in the art that modifications may be made to the various embodiments of the invention described without departing from the spirit of the invention or scope of the appended claims set forth below.

Each reference cited herein is hereby incorporated by reference in its entirety.

What is claimed is:

1. A method for the sequencing of a target nucleic acid comprising:
   a) performing a multistage mass spectrometry, comprising
      i) ionizing said target nucleic acid,
      ii) measuring the mass of the ionized target nucleic acid,
      iii) determining the base composition corresponding to the mass of said ionized target nucleic acid,
      iv) fragmenting said ionized target nucleic acid by a collision induced dissociation (CID),
      v) measuring the corresponding mass spectrum of the CID fragments, and
   b) comparing the measured CID mass spectrum of the target nucleic acid measured in step v) with a fraction of all calculated CID mass spectra, wherein each of said calculated CID mass spectra correspond to a base sequence having the base composition determined in step iii),
   wherein the comparison of the measured CID mass spectrum with the calculated CID mass spectra of step b) is performed by an optimization algorithm comprising the evolution steps of:
      aa) choosing a population of parent sequences all having said base composition determined in step iii),
      bb) selecting a fraction of parent sequences from said population of parent sequences, wherein the selection of said fraction of parent sequences is based on the comparison of score values of the calculated CID mass spectra of said population of parent sequences with respect to said measured CID mass spectrum measured in step v),
      cc) producing a population of daughter sequences comprising said fraction of parent sequences and altered sequences obtained by recombination of parent sequences from said fraction of parent sequences, said recombination being performed by exchanging a group of bases between two selected parent sequences of said fraction of parent sequences selected in step bb), wherein said group of bases has the same base composition and
      dd) repeating steps aa) to cc), wherein said population of daughter sequences produced in step cc) is used as the population of parent sequences for the next evolution step,
   wherein said optimization algorithm compares said measured CID mass spectrum successively with said plurality of calculated CID mass spectra and determines a respective score value for each comparison, said score value representing the degree of consistency between said measured CID mass spectrum and said calculated CID mass spectra, and
   wherein the base sequence corresponding to the calculated CID mass spectra yielding the best score value is selected as the base sequence of said target nucleic acid, and said base sequence is presented in a user readable format.

2. The method according to claim 1, wherein said target nucleic acid is amplified prior to performing said multistage mass spectrometry in step a).

3. The method according to claim 1, wherein said target nucleic acid is separated from other components of the sample prior to performing said multistage mass spectrometry in step a).

4. The method according to claim 3, wherein the separation is performed by liquid chromatography or capillary electrophoresis and wherein said separation is performed in an offline or an online fashion.

5. The method according to claim 1, wherein the ionization in step i) is an electrospray ionization, a desorption electrospray ionization, a matrix-assisted laser desorption ionization or a fast atom bombardment.

6. The method according to claim 1, wherein the multistage mass spectrometry (MS) is performed by ion-trap MS, triple quadrupole MS, time of flight (TOF) MS, quadrupole TOF MS, Fourier transform MS or combinations thereof.

7. The method according to claim 1, wherein said fraction of parent sequences selected in step bb) comprises between 30% and 80% of said population of parent sequences.

8. The method according to claim 1, wherein said fraction of parent sequences selected in step bb) comprises between 40% and 60% of said population of parent sequences.

9. The method according to claim 1, wherein said population of daughter sequences has the same size as said population of parent sequences.

10. The method according to claim 1, wherein said group of bases comprises between 10-60% of the complete parent sequences.

11. The method according to claim 1, wherein a fraction of the daughter sequences of said population of daughter sequences produced in step cc) is altered by mutation prior to the next evolution step, wherein 2 or more bases within one daughter sequence are exchanged.

12. The method according to claim 11, wherein 10-80% of said daughter sequences are altered by mutation.

13. The method according to claim 1, wherein if in step iii) more than one base composition is determined to correspond to the mass of said ionized target nucleic acid measured in step ii), the comparison of step b) is performed for each of the determined base composition, the base sequences having the best score value for each of said base compositions are obtained and the base sequence having the best score value of all of said base compositions is selected as the base sequence of said target nucleic acid.

14. The method according to claim 1, wherein if in step iii) more than one base composition is determined to correspond to the mass of said ionized target nucleic acid measured in step ii), all of said determined base compositions are used for the comparison in step b).

15. The method according to claim 1, wherein the calculated CID mass spectra are obtained using the theoretical fragmentation scheme of collision induced dissociation of nucleic acids.

16. The method according to claim 1, wherein said sequencing of the target nucleic acid is a de-novo sequencing.

17. The method according to claim 1, wherein for target nucleic acids with a length of more than 30 bases, the additional step of fragmenting the target nucleic acids into subsequences having a length of not more than 30 bases, is performed prior to performing said multistage mass spectrometry in step a), wherein for each of said subsequences a base composition is determined in step iii) and a CID mass spectrum is measured in step v) and wherein the base sequences corresponding to the calculated CID mass spectra each yielding the best score value for the respective subsequences are the base sequences of said subsequences.

18. The method according to claim 17, wherein the step of fragmenting a)iv) is performed by enzymatic digestion.

19. The method according to claim 18, wherein said enzymatic digestion is performed using an enzyme of the RNaseIII family, a Dicer enzyme or a restriction enzyme.

20. The method according to claim 17, wherein an amplification reaction of said target nucleic acid is performed prior to the step of fragmenting a)iv), wherein said amplification reaction is performed with deoxyribonucleotides (dNTP), ribonucleotides (NTP) and an engineered polymerase having the ability to incorporate both dNTPs and NTPs and wherein said step of fragmenting a)iv) is performed by an alkaline hydrolysis.

21. The method according to claim 17, wherein the base sequences of said subsequences are used to reconstruct the base sequence of said target nucleic acid.

22. The method according to claim 20, wherein the sequencing of the target nucleic acid is a de-novo sequencing of said target nucleic acid comprising aaa) performing at least two different amplification reactions of said target nucleic acid, wherein in each of said different amplification reactions one of the 4 dNTPs is replaced by the corresponding NTP, bbb) analyzing each of the different amplification products of said at least two different amplification reactions separately, wherein each of said different amplification products is fragmented by an alkaline hydrolysis step prior to the multistage mass spectrometry and ccc) using the base sequences of all subsequences obtained by the analysis of the different fragmented amplification products to reconstruct the base sequence of the target nucleic acid.

23. The method according to claim 22, wherein three or four different amplification reactions are performed.

24. The method according to claim 22, wherein more than one different engineered polymerases are used.

25. The method according to claim 22, wherein for each of said different amplification reactions a different engineered polymerase is used.

26. The method according to claim 1, wherein said multistage mass spectrometry is a tandem mass spectrometry.

* * * * *

SEQUENCE LISTING

```
<160> NUMBER OF SEQ ID NOS: 8

<210> SEQ ID NO 1
<211> LENGTH: 14
<212> TYPE: DNA
<213> ORGANISM: Artificial
<220> FEATURE:
<223> OTHER INFORMATION: target

<400> SEQUENCE: 1
gagactgcca agcg                                                      14
```

<210> SEQ ID NO 2
<211> LENGTH: 87
<212> TYPE: DNA
<213> ORGANISM: Homo sapiens

<400> SEQUENCE: 2
ctgggagggt gtgtctcagt gtctatggct gtggttcggt ataagtctga gcatgtctgc        60
cagggtgtat tgtgcctgt atgtgcg                                             87

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
ctgggagggt gtgtctcagt                                                    20

<210> SEQ ID NO 4
<211> LENGTH: 21
<212> TYPE: DNA
<213> ORGANISM: Artificial
<220> FEATURE:
<223> OTHER INFORMATION: primer

<400> SEQUENCE: 4
cgcacataca ggcacaaata c                                                  21

<210> SEQ ID NO 5
<211> LENGTH: 25
<212> TYPE: DNA
<213> ORGANISM: Artificial
<220> FEATURE:
<223> OTHER INFORMATION: amplification fragment

<400> SEQUENCE: 5
ctgggagggt gtgtctcagt gtcta                                              25

<210> SEQ ID NO 6
<211> LENGTH: 16
<212> TYPE: DNA
<213> ORGANISM: Artificial
<220> FEATURE:
<223> OTHER INFORMATION: amplification fragment

<400> SEQUENCE: 6
tggctgtggt tcggta                                                        16

<210> SEQ ID NO 7
<211> LENGTH: 12
<212> TYPE: DNA
<213> ORGANISM: Artificial
<220> FEATURE:
<223> OTHER INFORMATION: amplification fragment

<400> SEQUENCE: 7
tttgtgcctg ta                                                            12

<210> SEQ ID NO 8
<211> LENGTH: 22
<212> TYPE: DNA
<213> ORGANISM: Artificial
<220> FEATURE:

-continued

<223> OTHER INFORMATION: amplification fragment

<400> SEQUENCE: 8
cgcacataca ggcacaaata ca                                              22